(12) United States Patent
Robergé et al.

(10) Patent No.: US 7,043,426 B2
(45) Date of Patent: May 9, 2006

(54) STRUCTURED SPEECH RECOGNITION (75) Inventors: James Robergé, Darien, IL (US); James Wolfer, Berrien Springs, MI (US); Jeffrey Soble, Highland Park, IL (US)

(73) Assignee: Cyberpulse, L.L.C., Highland Park, IL (US)

(*) Notice: Subject to any disclaimer, the term of this patent is extended or adjusted under 35 U.S.C. 154(b) by 734 days.

(21) Appl. No.: 09/939,392

(22) Filed: Aug. 24, 2001

(65) Prior Publication Data

US 2002/0072896 A1 Jun. 13, 2002

Related U.S. Application Data

(63) Continuation-in-part of application No. 09/584,925, filed on May 31, 2000, now Pat. No. 6,381,611, which is a continuation of application No. 09/053,304, filed on Apr. 1, 1998, now Pat. No. 6,154,750.

(60) Provisional application No. 60/241,199, filed on Oct. 17, 2000.

(51) Int. Cl.
*G10L 15/00* (2006.01)

(52) U.S. Cl. ............... 704/231; 704/9; 704/7; 704/10

(58) Field of Classification Search ............ 705/2; 382/225, 230; 704/4, 7, 9–10, 257, 275, 704/270
See application file for complete search history.

(56) References Cited

U.S. PATENT DOCUMENTS

| | | | |
|---|---|---|---|
| 5,226,117 A | 7/1993 | Miklos | |
| 5,241,624 A | 8/1993 | Torres | |
| 5,247,666 A | 9/1993 | Buckwold | |
| 5,263,174 A | 11/1993 | Layman | |
| 5,307,262 A | 4/1994 | Ertel | |
| 5,379,422 A | 1/1995 | Antoshenkov | |
| 5,412,776 A | 5/1995 | Bloomfield et al. | |
| 5,425,140 A | 6/1995 | Bloomfield et al. | |
| 5,504,850 A | 4/1996 | Aoyama | |
| 5,715,449 A | 2/1998 | Peters, Jr. et al. | |
| 5,774,588 A * | 6/1998 | Li | 382/230 |
| 5,801,702 A | 9/1998 | Dolan et al. | |
| 5,809,476 A * | 9/1998 | Ryan | 705/2 |
| 5,812,134 A | 9/1998 | Pooser et al. | |
| 5,812,135 A | 9/1998 | Kotchey | |
| 5,890,103 A | 3/1999 | Carus | |
| 5,905,498 A | 5/1999 | Diament | |
| 5,940,831 A | 8/1999 | Takano | |
| 5,950,168 A | 9/1999 | Simborg et al. | |
| 5,953,017 A | 9/1999 | Beach et al. | |
| 5,953,724 A | 9/1999 | Lowry | |

(Continued)

*Primary Examiner*—W. R. Young
*Assistant Examiner*—Huyen X. Vo
(74) *Attorney, Agent, or Firm*—Fitch, Even,Tabin & Flannery (57) ABSTRACT

Speech recognition methods, systems, and interfaces are used in the generation of medical reports from data in a hierarchically-organized database for the entry and searching of data in a database based on spoken utterances of a user. A workflow function facilitates a series of contexts, typically based on information in a knowledge base, that are used to establish procedural rules and word-mapping databases for each context for word-matching data entry based on spoken utterances of a user. The generation of medical reports from the entered medical data provides for searching the database generated using the speech recognition methods. The series of contexts and word-mapping databases are developed using a hierarchically-organized database representation based on knowledge regarding the relationship of data items in the main database.

13 Claims, 6 Drawing Sheets

U.S. PATENT DOCUMENTS

| | | |
|---|---|---|
| 5,970,460 A | 10/1999 | Bunce et al. |
| 6,058,366 A | 5/2000 | Tarkiainen et al. |
| 6,085,160 A | 7/2000 | D'hoore et al. |
| 6,131,098 A | 10/2000 | Zellweger |
| 6,137,911 A * | 10/2000 | Zhilyaev .................... 382/225 |
| 6,154,750 A | 11/2000 | Robergé et al. |
| 6,185,524 B1 | 2/2001 | Carus et al. |
| 6,260,013 B1 | 7/2001 | Sejnoha |
| 6,272,463 B1 | 8/2001 | Lapere |
| 6,275,802 B1 | 8/2001 | Aelten |

* cited by examiner

STRUCTURED SPEECH RECOGNITION

CROSS-REFERENCE TO RELATED APPLICATIONS

This application claims benefit of U.S. Provisional Application No. 60/241,199, filed Oct. 17, 2000, and this application is a continuation-in-part of prior application Ser. No. 09/584,925, filed May 31, 2000 now U.S. Pat. No. 6,381,611, which is a continuation of prior application Ser. No. 09/053,304, filed Apr. 1, 1998 now U.S. Pat. No. 6,154,750.

BACKGROUND OF THE INVENTION

1. Field of the Invention

This invention relates to methods for entry, update, and review of data into databases and generation of medical reports using speech recognition methods.

2. Description of the Related Art

Currently available commercial speech recognition engines work in two fundamental modes: command/control and dictation. The command and control engines constrain the speech to be composed of a set of pre-defined utterances that are defined by a context-free grammar. They must be spoken exactly in order to be recognized. Since this limits the set of utterances that can be recognized it tends to increase accuracy. Dictation modes relax this constraint, allowing relatively unconstrained speech recognition, at the expense of the ability to automatically identify the beginning and end of a logical entry, speed, and recognition accuracy.

Unfortunately, neither of the currently available speech engine modes is adequate for speech recognition in the context of medical record database data entry and medical report generation. Medical records speech recognition systems require the large degree of the flexibility available from a dictation engine coupled with the speed and accuracy of the command and control engine, as well as the ability to associate an utterance with its specific database counterpart. Currently there is a need for such a system.

Furthermore, current speech recognition systems for entry of data into databases that allow unconstrained entry of words, do not provide databases that are ideally-suited for searching. This conclusion is based on the fact that data is not entered uniformly into the database in these systems. Therefore, a database entry of the same information may be represented differently by different users of the database. Searching for this information becomes problematic because of the non-uniformity of the resulting data set—in essence, database search reduced to a text search of the recorded dictation. Therefore, there is a need for methods and systems that allow a user to enter information in an unconstrained manner, but standardize the information so that the same information is coded and stored in an identical manner in the database to facilitate searching.

In order to meet this need the current invention takes advantage of specific knowledge regarding the relatedness of fields within a database, and the expected information to be entered into the database, to allow for relatively natural speech within a predefined context. The methods are particularly well-suited for medical records database data entry and medical report generation.

SUMMARY OF THE INVENTION

The systems of the current invention weaken the accuracy of a command-and-control approach by creating a grammar consisting of the individual words, typically occurring in a knowledge base context, then compensating for inaccuracies in the resulting speech recognizer by exploiting the knowledge contained in the knowledge base through a scoring mechanism. This allows the association of commercial speech recognizer results with specific knowledge base entries quickly and accurately.

The current invention provides speech recognition methods, systems, and interfaces that facilitate the entry and searching of data in a database based on spoken utterances of a user. In certain preferred embodiments, the database is a medical records database. In a preferred aspect the current invention provides the generation of medical reports from the entered medical data. In another preferred aspect, the current invention provides methods for searching the database generated using the speech recognition methods of the current invention.

The methods and systems of the current invention involve developing a series of contexts. Typically, each context is represented by a context identifier. For each context, a word-mapping database is created based on information, typically at least some of which is based on spoken phrases, which is likely to be entered for the various data items within the context. During runtime, a context is selected and a set of data items within the context is then populated by mapping the speech recognition output generated based on utterances of the user to data items in the main database for the selected context using the word-mapping database, where this step may also include the processing of local navigational commands within the context. Finally, additional contexts are identified and their associated selected data items populated as above until the user completes their entries and the main database is populated with the recorded data.

In preferred embodiments, the series of contexts are generated using a hierarchically-organized database representation (i.e. a knowledge base) based on knowledge regarding the relationship of fields in the main database. Preferably, the hierarchically-organized database representation has a plurality of nodes capable of having further related nodes, fields, or attributes.

Preferably, the main database is a medical records database and the series of contexts are developed based on completion of data entry for generation of a medical report.

BRIEF DESCRIPTION OF THE DRAWINGS

FIG. 5 illustrates the resulting display screen for an exemplary embodiment of the current invention after the user uttered the phrase "moderate to severe stenosis."

DETAILED DESCRIPTION OF THE PREFERRED EMBODIMENT

In presenting a detailed description of the preferred embodiment of the invention, examples are used that are based on a very simple clinical database. These examples are provided to illustrate certain elements of the invention. They are not to be construed as limiting the invention in any way. The speech entry system consists of a suite of functions that include knowledge extraction, grammar formation, speech engine control, and knowledge base entry association.

Figure 1:
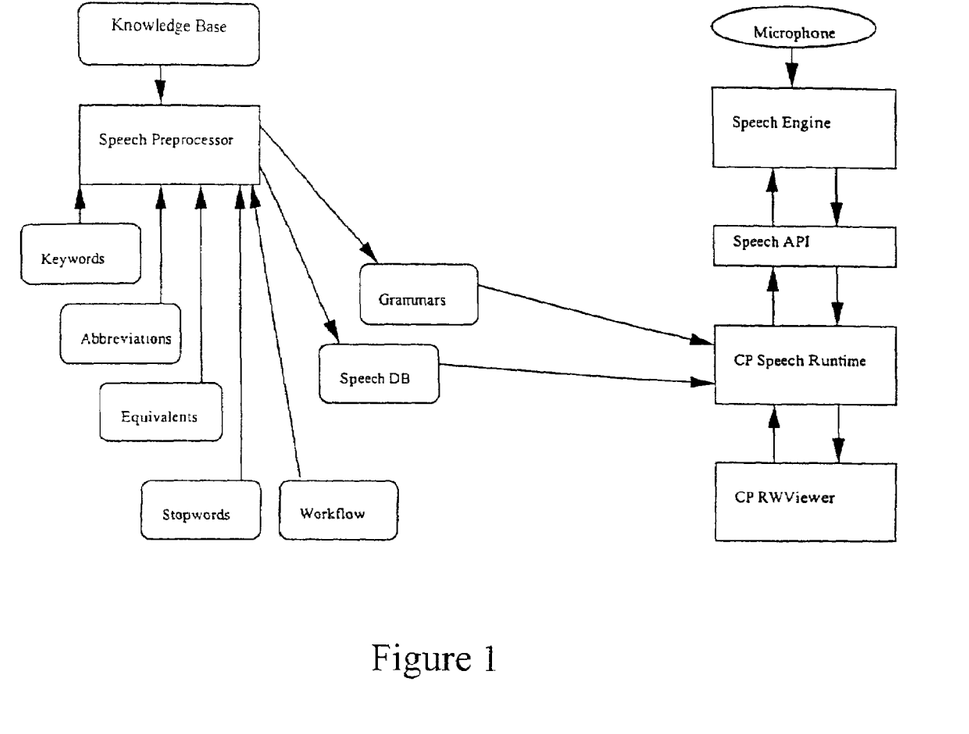
FIG. 1 shows a block diagram of a preferred embodiment of the basic system of the current invention.

FIG. 1 shows a block diagram of a preferred embodiment of the basic system of the current invention. The Speech Preprocessor function acts to extract and organize information needed at run-time. Input to the speech preprocessor includes a workflow function that specifies groups of findings grouped to enhance workflow, to establish a vocal context, and to establish a set of procedural and navigational commands. The preprocessor allows the "voice knowledge engineer" (the engineer creating the knowledge base tuned for voice) to create any arbitrary set of findings from the knowledge base into a "workflow". There may be many defined "workflows", and they may contain overlapping findings. Thus the "voice knowledge engineer" can create a set of "workflows" that best matches the needs and style of a target customer class. For example, the workflow for a Cardiologist may be based on anatomical structure (i.e., left ventricle, mitral valve, etc.) while the workflow for a Radiologist may be based upon pathology (e.g., lesion type, etc.). Once defined, for each entry in the workflow, a set of navigational commands a word-mapping database, and a vocal grammar are constructed.

A number of additional features/functions are provided to the speech processor in preferred embodiments. With reference to FIG. 1, the right side of panel 10 provides a prompting script used to remind the novice user of some of the valid utterances. Several features also are set forth to facilitate structured speech recognition. For example, in the present described embodiments a set of stop words is input to the speech processor. Stop words are words that are recognized as valid utterances but which are ignored by the system when extracting content. In the word-mapping database, stop words are not simply used for content extraction. Examples of such words are: the, an, and to. It is important to be able to say these words in the system, but these words do not add much "content" to the utterance. In certain preferred embodiments, keywords are provided to the speech preprocessor. Keywords are identified for any knowledge base entry and are used to remove ambiguity within the database. Additionally, certain embodiments include a set of standard abbreviations for knowledge base entries. For example "ECG" is an abbreviation for electrocardiogram. Furthermore, certain preferred embodiments include a set of synonyms and equivalent phrases to substitute for identified phrases. For example "regurgitation" may be the equivalent of "insufficiency" in certain medical contexts.

Typically, for each group of findings defined in the Workflow specification, the preprocessor creates a word-mapping database consisting of the set of words allowed within that context, along with a set of common linking words (stop words). Each word is linked to the knowledge base phrases containing this word, along with the number of words identified as keywords for any given phrase or subphrase.

In addition to the functions described above, the preprocessor produces a set of grammars for the speech engine. Preferably, it has the flexibility to be easily modified to produce the grammars in various speech engine vendor specified formats. A grammar is a formal description in a format specified by a speech recognition engine manufacturer specifying the words and/or phrases that can be recognized. A speech recognition Engine is a commercial product, which takes spoken utterances and returns information representing the corresponding words.

Figure 2:
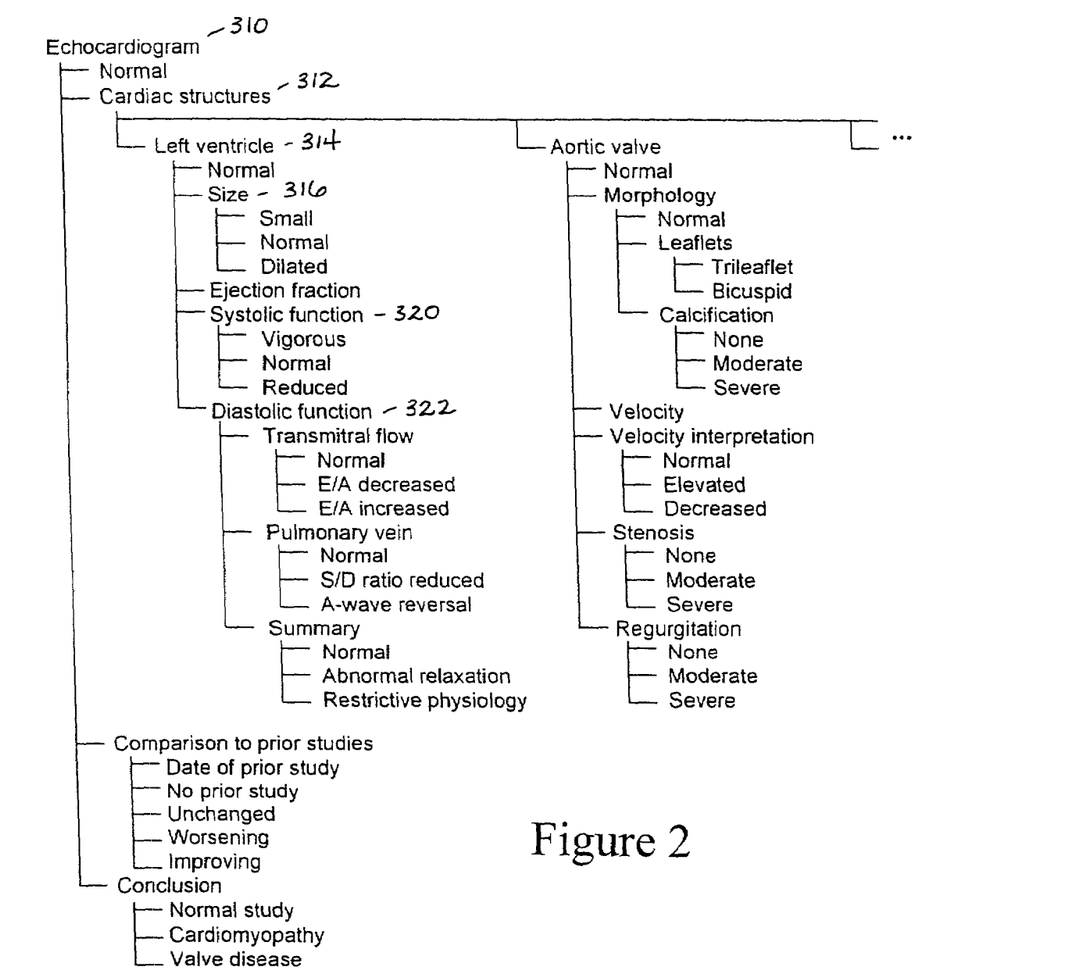
FIG. 2 provides a tree structure illustrating an example of a hierarchical knowledge base in accordance with a preferred embodiment of the invention.

In certain preferred embodiments, the workflow function uses a knowledge base to group findings, to establish procedural and navigational commands, to create word-mapping databases for grouped findings, and to facilitate transfer of data for specific fields of the main database based on comparison of speech recognition output to words of the word-mapping databases. FIG. 2, shows a knowledge base, a hierarchically-organized database representation. The organization of information and the information content of the knowledge base is based on specific knowledge related to the database and facilitates entry of data into the represented database. Strictly speaking a hierarchical organization is not necessary for the speech subsystem itself, the speech subsystem is working within this pre-existing context. The hierarchical structure is the representation chosen for representing the expert clinical knowledge in the present described system, and the power of the product derives from extracting speech information from this knowledge base.

Knowledge bases employed in the present described embodiment provides on the order of hundreds to thousands of natural language sentences that encapsulate knowledge related to a particular discipline, as well as fields that are populated by the sentences, and which correspond to database fields. FIG. 2 represents entries in the menu system. The speech system augments this by deriving the word-mapping databases and speech grammars from the set of potential sentences contained in the parent knowledge base. Thus FIG. 2 illustrates the structural organization of the database from which sentences would be subsequently constructed. As discussed further below, metrics are provided with scoring to facilitate information preprocessing.

In preferred embodiments, the knowledge bases of the current invention contain clinical knowledge. To allow for fast entry of clinical findings, the current system and methods associate a spoken utterance with its corresponding entry in the knowledge base using relatively unconstrained speech.

Consistent with accepted terminology in the field, a hierarchically-organized knowledge base may be referred to herein as a tree, the topmost node in the hierarchy as the root node, the path from the root node to any other node as a branch, and a subset of the hierarchy that is itself a hierarchy, as a subtree. Each leaf node in the knowledge base hierarchy represents an atomic data item. Each branch node represents either the root of a collection of related data items, or a navigational cue leading to data items (atomic or collected) situated below it in the hierarchy.

The exemplary structure shown in FIG. 2 provides the echocardiogram aspects of a medical knowledge base (KB) being broken down as between normal, cardiac structures, comparison to prior studies, and conclusions. Conclusions are further segmented into data fields of the database associated with the hierarchical knowledge base as discussed further below.

The knowledge base hierarchy is typically organized according to anatomical structures, with detailed description of those structures organized into individual subtrees. Navigation for data entry in the user interface is done by verbally selecting a structure of interest or finding a structure of interest in the menu system or summary viewer, as described below.

Typically, there are several types of nodes in the knowledge base for entry using the menu system: (1) statement nodes which contain a complete statement as to their contents, which users select to record the proper value; (2) text or numeric entry forms that allow a user to enter a particular value for that node; and (3) combo boxes which are either leaf nodes that allow selection of a value for that node from a list of values, or nodes that allow a user to pick from a list of leaf nodes.

Returning again to FIG. 1, the run-time system manages the speech engine, coordinates context and grammar switching as necessary, interprets the results returned by the speech engine responding to user utterances, and interfaces to an automated viewer function, such as the Cyberpulse Report Wizard™ Viewer.

Once the system is initialized, the user utters a statement into the microphone. The vendor supplied speech engine communicates the recognition results to the speech runtime function through a defined Application Program Interface.

Next, the speech runtime function takes the information returned by the speech engine, places it within the proper procedural and navigational context, and, if appropriate, compares words contained in the information to the word-mapping database created for the context, and extracts the appropriate finding to enter into the main database. In order to provide for a flexible natural language interface that is not highly dependent on word order, a hierarchically scored matching system is augmented with statistical information from the preprocessor described above, as well as metrics ascertained at run-time, to resolve sequential word-ordering differences. "Statistical information from the preprocessor" refers primarily as the base number of keywords in each recognizable sentence or phrase which is calculated once in the preprocessing stage. "Metrics ascertained at run time" simply refers to the scoring system described as follows: 1) keywords are weighted in importance; and 2) "Longest Common Substring" as an additional disambiguator.

In preferred embodiments, the hierarchically scored matching system provides at least one of the following scoring levels, and preferably all 3 scoring levels, most preferably in a hierarchical manner as described below, to identify a matching data item from the knowledge base. Level-1 scoring provides keeping a score, for each possible data item, of the number of keywords in the associated phrase (or sentence) that were actually recognized in the utterance to generate a keyword match number. Level-2 scoring provides computing the ratio of keywords hit to total keywords associated with a data item to generate a keyword match ratio. Level-3 scoring utilizes a string searching algorithm, which in preferred embodiments calculates the Edit Distance, also referred to as the Levenshtein Distance, between the uttered phrase and the knowledge base phrases associated with a data item. ("Algorithms in Detail" and "Core String Edits, Alignments, and Dynamic Programming," Chapters 3.2 and 11, respectively, in *String Searching Algorithms*, World Scientific Publishing Co., River Edge, N.J. (1994). Edit Distance as used in the current application is a metric of the relative similarity of two strings of words: Intuitively, the minimum number of specified editing operations necessary to transform one string into the other. Id.

As an example of a metric analysis, assuming the user uttered, e.g., "There was a left to right shunt." Using only the keyword hits/ratios each of the following sentences in the data base would score identically:
    There was a left to right shunt.
    There was a right to left shunt.

Assuming left, right, and shunt were the keywords, each potential match would have a score of three and a ratio of 1.0 (all keywords hit). Thus the system would, at this point, still have two potential matches. To help disambiguate this situation, we find the Edit distance between each candidate and the uttered phrase. Assuming that we do this on the word level (as opposed to character-by-character) we will be computing the edit distances for the following cases:
    Case A:
    There was a left to right shunt (our utterance)
    There was a left to right shunt (our first potential match)
    Case B:
    There was a left to right shunt (our utterance)
    There was a right to left shunt (our second potential match)

Case A will have an edit distance of zero since no changes are necessary to convert the utterance into the potential match. Case B will have an edit distance of two, since there will be a minimum of two operations to transform the utterance into the potential match, namely substituting "left" for "right" in one position, and "right" for "left" in the other. Since the Edit distance for Case A (0) is less than that for Case B (1), we will assume that the sentence in Case A represents a closer match to the user's utterance, and we will choose that as the highest scoring entry.

Although any of these scoring approaches may be used alone or in combination, in preferred embodiments, Level-1 scoring is performed first. In the case of multiple knowledge base phrases containing the same Level-1 score, the Level-2 score is used to supplement the Level-1 score. In the case that Level-1 and Level-2 scores do not identify a best-fit phrase, which is most likely to occur in an order dependent word sequence, Level-3 Scoring is used.

Figure 3:
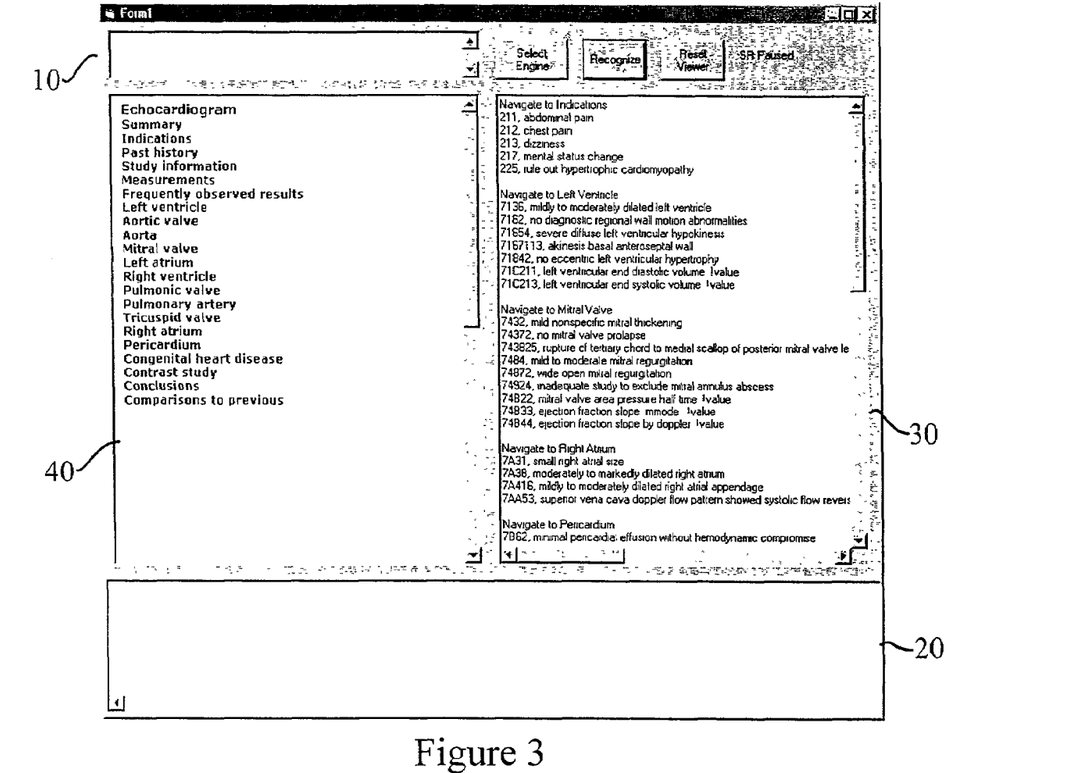
FIG. 3 displays a screen for an exemplary embodiment initialized and waiting for input.

Based upon the composite score returned, the set of best-matching findings (data items) from the knowledge base is identified and made available for subsequent processing for appropriate recording. There are two basic reasons for "set" instead of "single finding" here:
  1) If the speaker did not say enough to uniquely isolate a specific finding then the set of equally scored findings is returned. The speaker is then notified that the system was not able to determine which finding was appropriate. For example, assume the following two entries were in the database:
      Mild mitral calcification
      Mild perivalvular calcification
      and the speaker uttered "mild calcification". In this case both would score exactly the same and the system would have no way of knowing which was desired. So the set would be returned and the speaker basically asked "Which one do you mean?".
  2) In the case of a sentence identified as a "compound" sentence, where several findings are embedded into a single utterance, then the set of matching findings is returned and each one recorded. For example:
      There was <1>regurgitation of the <2>, where <1>=mild, moderate, etc. and <2>=mitral valve, tricuspid valve, etc. If the speaker said: "There was mild regurgitation of the tricuspid valve", the system would return the set:
      Finding 0: There was <1>regurgitation of the <2>
      Finding 1: <1>=mild
      Finding 2: <2>=tricuspid valve The following dialog and screen snapshots illustrate a preferred embodiment of the current invention. FIG. 3 displays a screen for an exemplary embodiment initialized and waiting for input. The small, currently empty, panel 10 on the upper left will contain the current workflow context. The large empty panel 20 on the bottom will contain the returned command to process or finding (data item) to record in the main database. The large panel 30 on the right is simply for engineering feedback. The large panel 40 on the left side contains an exemplary viewer.

Figure 4:
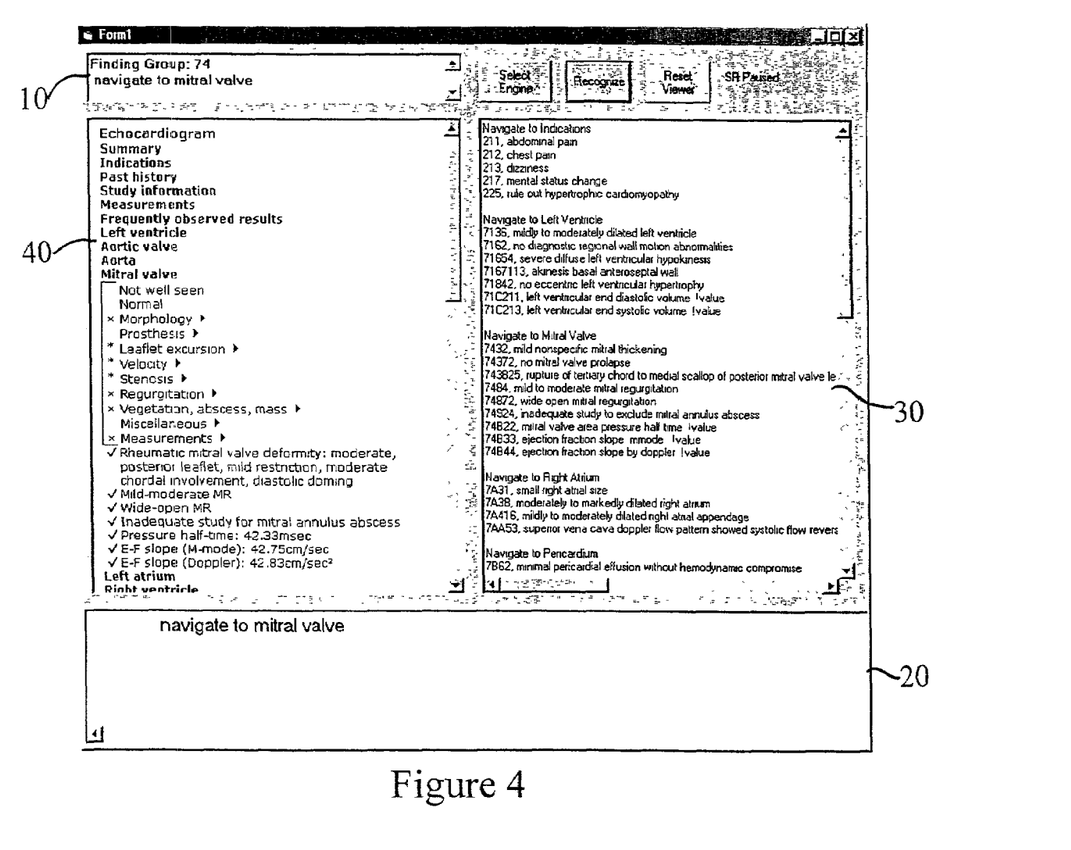
FIG. 4 illustrates the resulting display screen for an exemplary embodiment of the current invention after the user uttered the phrase "navigate to mitral valve."

At this point the phrase "Navigate to mitral valve" is uttered by the user. The results are illustrated in FIG. 4. The system recognized that "navigate to mitral valve" was the appropriate command (indicated in the large panel 20 at the bottom), and executed that command to set the current Finding Group to Mitral Valve. This is reflected in the small panel 10 in the upper left. The word-mapping database may be constructed for any level of detail desired and dynamically switched at run-time. In the illustration referred to here, each finding group has its own word-mapping database and corresponding grammar for the speech recognition engine to help improve recognition accuracy. However, here is no inherent limit to the number or extent of these word-mapping databases or the corresponding grammars.

Also the exemplary viewer 40 synchronized to mitral valve and indicates previously recorded findings with a check mark.

Subsequently uttering the phrase "moderate to severe stenosis" triggers the results shown in FIG. 5. Note that the viewer now shows a check mark by Moderate-severe, under the Mitral-Valve-Stenosis outline, indicating that the user has successfully entered that finding. Also note that the word "mitral" was never uttered. There was enough contextual information to extract the finding without it. To illustrate the flexibility of the scoring system of the present invention consider that the following examples would also cause entry of "oderate to sever stenosis": "there was moderate to severe stenosis", or, "there appeared to be severe to moderate mitral valve stenosis", or "mitral stenosis was severe to moderate".

While the preceding example focused on medical clinical entries, the systems and methods of the current invention can be used in a wide-variety of other technology areas. The systems and methods are equally applicable to any system that contains a predefined set of possible entries. For example, they are applicable to inventory management and reconciliation. In this case the set of possible products could be entered into the database, and the count of items-on-hand could be spoken for any given items. Another example is to use the methods and systems of the current invention to construct legal documents containing boilerplate language for a legal practice.

In preferred embodiments, the systems and methods of the current invention include a user interface 40 window that provides the user the opportunity to enter data into the data base via a keyboard or other input device that is not based on speech recognition. Furthermore, in preferred embodiments, the methods and systems of the current invention generate a medical report. The interface 40 may be used interchangeably with the speech recognition system for data input.

Figure 6A:
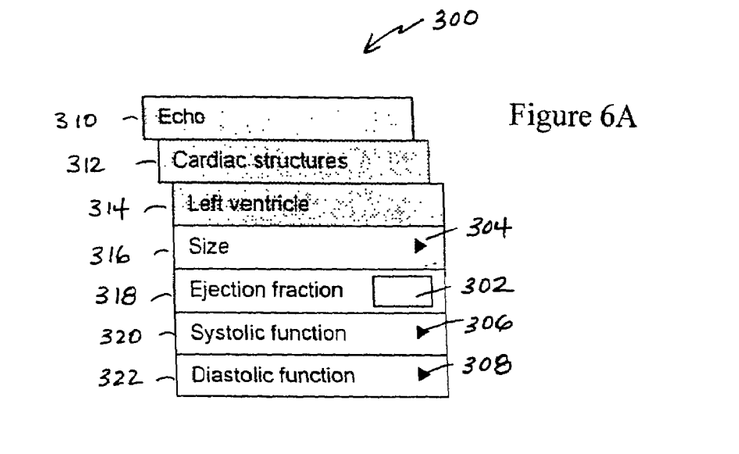
FIGS. 6A–C show the menu system, summary viewer, and graphical interface tool elements of an exemplary user interface provided for data entry review and navigation.

Preferred examples of the user interface for manual entry are provided in the left panel 40 of FIGS. 3–5 and in FIG. 6A. According to this preferred embodiment, navigation and data entry is provided by a menu-based system in addition to the speech recognition functions described above. The menu-based prompts facilitate data entry, for example by recording findings, triggering equations, and triggering macros, and for local navigation within the knowledge base. The contents of the pop-up menu may be context-sensitive or, alternatively, may be dynamic.

Figure 6B:
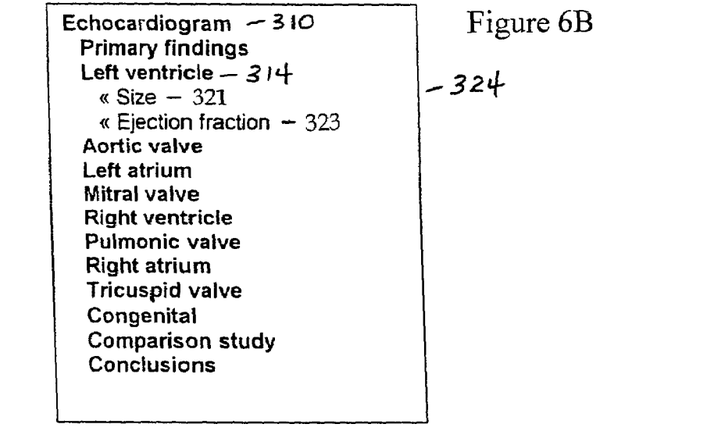

In certain preferred embodiments, as shown for example in FIG. 6B, the interface preferably includes a summary viewer in addition to the menu-based system described. The summary viewer contains text prompts that are used to review recorded data and for "global" navigation of the knowledge base via the finding group headings, shortcuts, and recorded findings, which may also function as shortcuts. A user may toggle between the menu system and summary viewer using a screen toggle object or by selecting menu items or summary viewer items. Most preferably, the menu system and summary viewer are embedded together in the same portion of the screen and used in a medical information context.

In certain preferred embodiments, the user interface facilitates direct visual cues using shortcuts and macros. Shortcuts allow the user to navigate quickly to frequently-used nodes in the knowledge base tree, whereas the menu system is typically exhaustive, i.e., containing all of the data elements and clinical content needed for any kind of report. The summary viewer contains text-based shortcuts that point to specific nodes in the knowledge base hierarchy. Macros define a series of related events that are initiated by selection of a triggering object on the keyboard user interface window.

Figure 6C:
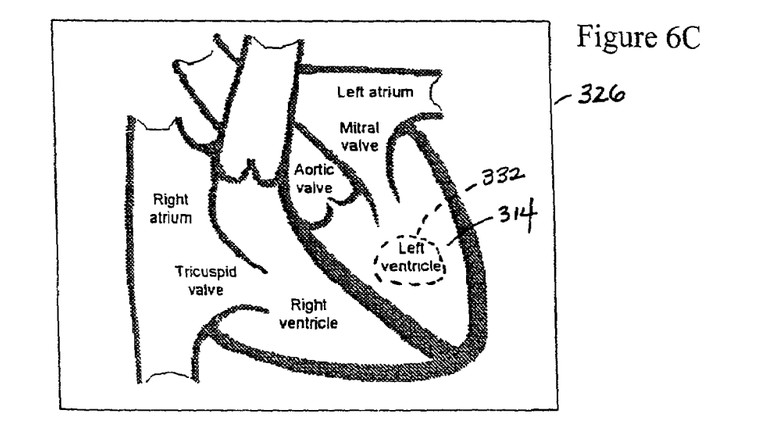

As exemplified in FIG. 6C, a graphical interface tool may be included in the keyboard user interface window. In certain preferred embodiments wherein the database populated by the current invention is a medical records database, the graphical interface may contain a portion of human anatomy. A user may select "hot spots;" on the graphical interface tool for "global" navigation and data entry by triggering macros. Typically, where the graphical interface tool is included, a user may toggle between the graphical interface tool, the menu system, and/or the summary viewer.

In addition to the data entry interface, preferred embodiments of the current invention provide a report generating function that automatically generates a set of reports from information entered in the data entry functions of the program. Most preferably the reports are medical reports that are formatted to visually appear similar or identical to reports generated by other methods and systems. For example, reports typically include a Demographics section, Summary section and a Detailed findings section. Other sections typical of a medical report may also be included in the report.

The report sections feature separates data organization used in the knowledge base from the organization of the information in the report. Typically, every finding in the knowledge base is associated with one or more report sections. Therefore, information may be tagged for its location within a report, in addition to its location within the database hierarchy. The knowledge base defines the sections that are available for the report, and then defines the sections for the data. In preferred embodiments, XML (extensible Markup Language) is used for tagging data entered by a user. The data contained in XML is preferably formatted using an XSL (eXtensible Style Language) stylesheet. This allows data that is displayed by tree path order and grouped into finding groups in the summary viewer to be displayed in any arbitrary layout within the report. It also allows data to be displayed in multiple sections or subsections within the report.

Certain embodiments of the methods and systems of the current invention include a database searching function (i.e. querying function). In addition to supporting data entry, the speech recognition and keyboard input interface provide an intuitive mechanism for specifying database queries on the data recorded from a knowledge base hierarchy. In query creation mode, the user navigates through the knowledge base hierarchy by selecting items from the menu system or by speaking commands in much the same manner as is done during data entry. However, selecting a recordable item (e.g., a leaf node) causes the creation of a query subexpression for that data item rather than the recording of the data item itself. The resulting query expression might be an SQL SELECT statement, or a set of SQL SELECT statements, that specify rules for retrieving the data item from a relational database. Any method known for querying databases can be used with the current invention. For example, but not intended to be limiting, the query might utilize an XSL rule set that retrieves the item from an XML representation of the recorded data (a set of report XML files). An important advantage of the query construction feature of the current invention is that the user does not need to be familiar with a query language to search the database.

The foregoing disclosure of embodiments of the invention has been presented for the purpose of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for populating a main database from speech recognition output based on verbal utterances of a user, said method comprising:
    a) developing a series of contexts, each context comprising a series of navigational commands for populating a selected series of data items of the main database, and each context represented by a context identifier;
    b) creating a word-mapping database for each context, said word-mapping database containing a words drawn from narrative statements (written and oral) associated with the data items in selected context, as well as linkages between these words and the data items;
    c) identifying a selected context by comparing the context identifier of the selected context with speech recognition output generated based on a context-identifying verbal utterance of the user;
    d) recording the selected data items within the selected context by mapping the speech recognition output generated based on utterances of the user to the data items in the main database using the word-mapping database for the selected context; and
    e) repeating steps c) and d) until the user finishes entering data, thereby populating the main database.

2. The method of claim 1, wherein the series of contexts and word-mapping databases are developed using a hierarchically-organized database representation based on knowledge regarding the relationship of data items in the main database, said hierarchically-organized database representation having a plurality of nodes capable of having further related nodes, fields, or attributes.

3. The method of claim 1, wherein the main database is a medical records database and the series of contexts are developed based on completion of data entry for generation of a medical report.

4. The method of claim 1, wherein speech recognition output is mapped to data items in the selected context using a word-mapping database that includes a set of designated keywords representing spoken phrases for populating data items and by comparing speech recognition output to these keywords.

5. The method of claim 4, wherein speech recognition output is compared to the words of the word-mapping database by:
    a) calculating the number of keywords in a phrase that match speech recognition output to generate a keyword match number;
    b) prioritizing phrases with identical keyword match numbers by calculating the ratio of keywords in a phrase that match speech recognition output to the total keywords in a phrase to generate a keyword match ratio; and
    c) prioritizing phrases with identical keyword match ratios by performing a string comparison algorithm.

6. The method of claim 4, wherein the word mapping is performed by calculating the number of keywords in a phrase that match speech recognition output, by calculating the ratio of keywords in a phrase that match speech recognition output to the total keywords in a phrase, or by performing a string comparison algorithm.

7. The method of claim 6, wherein the string comparison algorithm comprises the Edit Distance method.

8. A method for populating a main database from speech recognition output based on verbal utterances of a user, comprising:
    a) defining a workflow for populating a selected set of data items in the main database, each workflow providing custom knowledge comprising a series of navigational commands and a context identifier for associating spoken utterances with explicitly coded data relating to the workflows;
    b) identifying the workflow being employed;
    c) creating a word-mapping database for each workflow; and
    d) populating the selected series of data items for the identified workflow using the series of navigational commands and comparing speech recognition output generated based on the verbal utterances of the user to obtain words and explicitly coded data for populating the main database;
    wherein the defined workflows use the context identifier to provide metrics for scoring the selected context's speech recognition output based on the context-identifying verbal utterance of the user.

9. A method as recited in claim 8, wherein the defining of the workflows comprises developing a series of contexts for populating the selected data items in the main database with each context being represented by the context identifier.

10. A method as recited in claim 9, wherein the series of contexts are developed using a hierarchically-organized database representation.

11. A method as recited in claim 8, wherein the defined workflow comprises a medical records database and a series of context identifiers developed for the completion of a medical report.

12. A system for populating a main database from speech recognition output based on verbal utterances of the user, comprising:
    a context identifier for establishing a workflow for information processing of a series of navigational commands for populating a selected series of data items in the main database;

a word-mapping database created for each context identifier comprising words of possible entries of the data items in the context;

a processor for comparing information from the context identifier with speech recognition output generated based on a context-identifying utterance of the user;

a memory device associated with the main database for populating the selected series of data items for the selected context of the context identifier using the series of navigational commands and the speech recognition output;

wherein processor identifies the selected context associated with the context identifier using metrics for comparing the context identifier with the speech recognition output for generating scores associated with the context-identifying verbal utterance of the user.

13. A system as recited in claim 12, wherein said processor employs multi-level scoring for generating the speech recognition output.

* * * * *

UNITED STATES PATENT AND TRADEMARK OFFICE
CERTIFICATE OF CORRECTION

| | |
|---|---|
| PATENT NO. | : 7,043,426 B2 |
| APPLICATION NO. | : 09/939392 |
| DATED | : May 9, 2006 |
| INVENTOR(S) | : Robergé et al. |

It is certified that error appears in the above-identified patent and that said Letters Patent is hereby corrected as shown below:

IN THE CLAIMS:

Column 9, line 39, delete "a" after "containing".

Signed and Sealed this

Twenty-second Day of August, 2006

JON W. DUDAS
*Director of the United States Patent and Trademark Office*